United States Patent [19]

Hider et al.

[11] Patent Number: 4,894,455

[45] Date of Patent: Jan. 16, 1990

[54] PHARMACEUTICALLY ACTIVE ZINC COMPLEXES

[75] Inventors: Robert C. Hider, St. Osyth; George Kontoghiorghes; Jack Silver, both of London; Michael A. Stockham, Saffron Walden, all of England

[73] Assignee: National Research Development Corporation, London, England

[21] Appl. No.: 16,083

[22] Filed: Feb. 18, 1987

Related U.S. Application Data

[62] Division of Ser. No. 666,905, Oct. 31, 1984, Pat. No. 4,665,064.

[30] Foreign Application Priority Data

Oct. 31, 1983 [GB] United Kingdom ................ 8329043

[51] Int. Cl.$^4$ ................................. C07F 9/80
[52] U.S. Cl. ........................................ 546/2; 556/120; 556/125
[58] Field of Search ................ 518/184, 188; 556/120, 556/125; 546/2

[56] References Cited

U.S. PATENT DOCUMENTS

| | | | |
|---|---|---|---|
| 2,904,573 | 9/1959 | Oroshnik et al. | 260/439 |
| 3,130,204 | 4/1964 | Tate et al. | 260/345.9 |
| 3,236,733 | 2/1966 | Karsten et al. | 167/81 |
| 3,281,366 | 10/1966 | Judge et al. | 252/107 |
| 3,968,118 | 7/1976 | Lohans et al. | 260/297 Z |
| 4,018,907 | 4/1977 | Scarpellino | 426/250 |
| 4,225,614 | 9/1980 | Hansson | 424/289 |
| 4,279,936 | 7/1981 | Jones et al. | 426/265 |
| 4,442,305 | 4/1984 | Weitl et al. | 562/451 |
| 4,543,213 | 9/1985 | Weitl et al. | 260/239 BC |
| 4,575,502 | 3/1986 | Hider et al. | 514/184 |
| 4,575,502 | 3/1986 | Hider et al. | . |
| 4,587,240 | 5/1986 | Hider et al. | 514/188 |

FOREIGN PATENT DOCUMENTS

| | | |
|---|---|---|
| 94149 | 11/1983 | European Pat. Off. . |
| 107458 | 5/1984 | European Pat. Off. . |
| 2117766A | 10/1983 | United Kingdom . |
| 2118176A | 10/1983 | United Kingdom . |
| 2128998A | 5/1984 | United Kingdom . |
| 2136806A | 9/1984 | United Kingdom . |
| 2136807A | 9/1984 | United Kingdom . |

OTHER PUBLICATIONS

Reedijk et al—Recueil des Travaux Chimiques des Pays Bas et de la Belgique, 1972, vol. 91, pp. 681–687.
Gerard et al—Journal of Chemical Research, 1978 (M) pp. 4175–4186 and (S) 404–405.
Morita et al—Bulletin of the Chem. Soc. of Japan, 1976, vol. 49, pp. 2461–2464.
Stünz et al—Australian Journal of Chem., 1979, vol. 32, pp. 21–30.
Evans—Biological Aspects of Metals and Metal-Related Deseases (Ed. B. Sparken) New York 1983, pp. 81–88.
Bull. Soc. Chim. (1979), No. 11–12, pp. I-451 to I-456.
J. Chem. Res. (1978), (M), pp. 4875–4886 and (S),. 404–405.
J. Am. Chem. Soc. (1957) vol. 79, pp. 1296–1297.
Bull. Chem. Soc. Japan (1976) vol. 49, pp. 2461–2464.
Bull. Soc. Chim. France (1967), No. 8, pp. 2920–2923.
CA 68:8872k.
CA 77:101817s.
Solomons "Nutritional . . . of Zinc" Symposium Series Am. Chem. Soc., 1983, vol. 210, pp. 247–271.
CA 89:35629b.
Am. J. Dis. Child (1983) vol. 137, pp. 433–437.
Aggett et al, "Zinc Deficiency in Human Subjects" (1983) pp. 117–124.
Prasad "Biological Aspects of Metal . . . "(1983) pp. 107–119.
"The Economist" (1984) (Mar. 24) pp. 82–83.
Symposium Proceedings, Bethesda, MD (1975) pp. 137–173.
Aust. J. Biol. Sci., 1976, 29, pp. 189–196.
Croatica Chemica Acta CCACAA, 1973, 45, pp. 603–610.
J. Chem. Soc., Dalton Trans., (1982) pp. 1433–1438.
Ann. Chim., (Rome), vol. 66, Nos. 7–8, 1976, pp. 401–415.
Rec. Trav. Chim., 65:65 (1946).
CA 97:173875.
CA 87:157681s.
J. Chem. Soc., 69:1801 (1947).

(List continued on next page.)

*Primary Examiner*—Leonard Schenkman
*Attorney, Agent, or Firm*—Oblon, Spivak, McClelland, Maier & Neustadt

[57] ABSTRACT

Zinc(II) complexes in which at least one ligand is provided by a compound being:

(1) 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms; or (2) a 3-hydroxypyrid-2-one or 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or, except in the case of ionizable groups, more than one substituent selected from aliphatic acyl, alkoxy, aliphatic amine, aliphatic amide, carboxy, aliphatic ester, halogen, hydroxy and sulpho groups and, optionally, in which one or more of the hydrogen atoms attached to ring carbon atoms are replaced by one of said substituents, by an aliphatic hydrocarbon group of 1 to 6 carbon atoms, or by an aliphatic hydrocarbon group substituted by an alkoxy, aliphatic ester, halogen or hydroxy group; are of value in medicine, particularly in the systemic treatment of zinc depletion. Mixtures of these zinc complexes with the metal-free compound(s) providing the ligands contained therein and with iron(III) complexes containing ligands of types (1) and (2) are also of value.

39 Claims, No Drawings

OTHER PUBLICATIONS

*Helvetica Chimica Acta,* vol. XXIX, Fasciculus XII (1946), pp. 1669–1675.
Yakugaku Zasshi *J. Pharm.,* 90 (10):1222–5 (1970).
*Tetrahedron* (1970), vol. 26, pp. 3779–3785.
*J. Bacteriology,* (Jan. 1980) vol. 141, No. 1, pp. 164–168.
*CA* 85:56109q.
Tolanta (1974), 21, pp. 763–769.
*Chem. Abst.* vol. 75, No. 18 (Nov. 1, 1971) 115362k.
Martindale, the Extra Pharmacopoeia, The Pharm. Press, 1973, pp. 81 and 739.
Pitt and Gupta, Development of Iron Chelators for Clinical Use, Anderson and Hiller (EPS), 1975, pp. 137–173.
*Pfizer Tech. Bulletin,* Data Sheet No. 04/A/Mar., 1974.
*Pfizer Tech. Bulletin,* No. 865.
*Chem. Abst.* 94, 1981, 4114j.
*Chem. Abst.* 94, 1981, 24201h.
*Biochem. Pharm.,* 29, 1980, 1275.
*J. Pharm. and Experim. Therapeutics,* 196, 1976, 478.
*Brit. Journal of Hematology,* 33, 1976, pp. 487–495, White et al.
*J. of Pharm. Sci.,* 61, 1972, 1209, Foye et al.
*Collection of Czech. Chemical Comm.,* 33, Feb. 5, 1968, pp. 4198–4124.
*Chem. Pharm. Bull.* (1980), 28(9), pp. 2570–2579.
*J. of Bacteriology,* Jan. 1980, pp. 164 et seq. Akers et al.
*Am. Journal of Clinical Nutrition,* Jan. 1964, pp. 47–51, Bothwell et al.
*J. of Coord. Chem.,* 8, 1978, p. 27, Habeeb et al.
*J. Chem. Research,* 1980, 314, Gerard et al.
*Nempo,* 18, 1970, 16–21.
*Merck Index,* 9th Ed. (1976) (Merck & Co. Rahway, N.J.), pp. 543–544.
*CA* 94:156749c.
*CA* 98:71930n.
*Manufacturing Chemist in Aerosol News* (May 1970), by E. Jones, "Production of Enteric Coated Capsules".
*CA* 97:92048a.
*Bol. Soc. Chil. Quim.* (1982) 27, pp. 122–124.
Lieberman, H. A. and Lachman, L.: Pharmaceutical Dosage Forms, vol. 3 (1982), Marcel Decker, pp. 165–167.
Maxton, D. G.; Thompson, R. P. H.; and Hider, R. C., "Report of Iron Uptake from Fe(III) (Maltol, Human Studies" (Jan. 1986).
Skikne, Feb. 14, 1986 Letter.
Blake, "Study to Compare the Effect of Iron Maltol . . .".
*Struct. Bonding* (Berlin) (1984), vol. 58, pp. 25–87.
*Mol Pharm.* (1977) 13, pp. 362–367.
*J. Med. Chem.* (1974) vol. 17, No. 1, pp. 1–5.
*CA* 87:157681s.
*CA* 97:173875v.
*J. Chem. Soc. Dalton Trans* (1982) pp. 1433–1438.
*J. Chem. Soc., Chem. Comm.* (1982) pp. 779–781.
*J. Inorg. Biochem.* (1982) vol. 16, pp. 21–32.
*Inorg. Chem.* (1983), pp. 480–485.
*J. Polym. Sci.: Pol. Chem. Ed.* (1976), vol. 14, pp. 2155–2165.
*J. Am. Chem. Soc.* (1979), vol. 101, pp. 6534–6541.
*J. Med. Chem.* (1979), vol. 22, pp. 1281–1283.
*J. Med. Chem.* (1980), vol. 23, pp. 1130–1133.
*Ann. N.Y. Acad. Sci.* (1981), pp. 425–435.
*Tet. Lett.* (1981), vol. 22, pp. 2739–2742.
*In. Chem.* (1982), vol. 21, pp. 2209–2215.
*J. Am. Chem. Soc.* (1981), vol. 103, pp. 5133–5140.
*In. Chem.* (1982), vol. 21, pp. 3437–3442.
*Biochem.* (1983), vol. 22, pp. 1621–1630.
*J. Pharm. Exp. Therap.* (1984), vol. 228, pp. 676–681.
*Rad. Research* (1984), vol. 99, pp. 85–105.
Itoh et al, "The Journal of Antibiotics", vol. XXXII, No. 11, pp. 1089–1095 (Nov. 1979).
Aktieselskabet (U.K. Patent 778,871).
Barker et al, *CA* 92:179021g.
The Journal of Antibiotics, vol. 32, No. 11, 1979, pp. 1096–1103.
Hider et al (U.K. Patent Application GBA 2117766).
Atkinson et al (U.S. Pat. No. 4,358,455).
McInnes et al, Journal of the Chemical Society, Chemical Communications, 1974, No. 8, 281–282.
Neilands, Science, 1967, 156, 1443–1447.
Dittmar et al, 1974, 17, 753–756.
Bernstein et al (U.S. 2,742,476).
Durbin, P. W. et al, "Kinetics of Plutonium Deposition in the Mours," Ann. Rpt. 1983–4, Biology and Medicine Division, Lawrence Berkeley Lab. (Apr. 1985).
Durbin, P. W. et al, "New Sequestering Agents for the Actinides . . . ," Ann. Rpt. 1983–4, Biology and Medicine Division, Lawrence Berkeley Lab.
Raymond, K. N., "Specific Sequestering Agents for Iron and Actinides," in *Environmental Inorganic Chemistry* (VCH Publishers, Inc. 1985).
Riley, P. E. et al, "Specific Sequestering Agents for the Actinides. 9. Synthesis of Metal Complexes of 1-Hydroxy-2-Pyridinone . . . , ".
*Inorganic Chemistry* 22 (1983), pp. 3940 et seq. This document discusses possible use of the HOPO group in iron(III) and actinide chelation.
Scarrow, R. C. et al, "Ferric Ion Sequestering Agents . . . ," *Inorganic Chemistry* 24 (1985), pp. 954 et seq.
Scarrow et al, *CA* 102:124493g.
Raymond et al, *CA* 103:192911n.
*CA* 92:130476r.
*CA* 64:3504d.
*CA* 93:130476r.
*CA* 75:115362k.
*CA* 94:41144j.
Weatherall et al. (eds.), Oxford Textbook Medicine, Ox. Univ. Press, vol. 1 (1983), p. 7.

PHARMACEUTICALLY ACTIVE ZINC COMPLEXES

This is a division, of application Ser. No. 666,905, filed Oct. 31, 1984 now U.S. Pat. No. 4,665,064.

This invention relates to zinc compounds and to various mixtures containing these compounds for use in pharmaceutical compositions, especially for the treatment of zinc depletion, and in foodstuffs.

An adequate supply of zinc to the body is an essential requirement for tissue growth in both man and animals. Moreover, a deficiency of zinc can produce various clinical effects, for example leading to skin lesions, alopecia and mental disturbance. Although there is normally an ample amount of zinc in the diet, the level of absorption of zinc from food is generally low so that the supply of zinc to the body can become critical under a variety of conditions. Zinc depletion is commonly encountered in the mother during pregnancy with consequent depletion of zinc in the foetal tissues together with idiopathic retardation of intrauterine growth. Certain diets may inhibit zinc absorption due to their phytic acid content, and many orally administered iron preparations can seriously inhibit zinc absorption.

Various preparations for the systemic treatment of zinc depletion are marketed but these contain zinc in the salt form, particularly as zinc sulphate, and the level of zinc uptake by the body from these preparations is often quite low thereby necessitating the administration of relatively high dosage levels. The administration of high dose, poorly absorbed, zinc salts can create various problems. Thus, zinc salts are generally astringent, causing irritation and toxicity to membrane tissue, and systemic treatment may be associated with a variety of side effects including nausea, vomiting, headache, myalgia, chills and fever. It should be noted that zinc sulphate and zinc acetate are recognised emetics.

The present invention involves the treatment of zinc depletion through the administration of zinc in complex, rather than salt form, utilising a group of zinc complexes which we have identified as being of particular value for use at relatively low dosage levels. The value of these complexes in this context was hitherto quite unrecognised and indeed, this is believed to be the first use of a complex for the treatment of systemic zinc depletion.

The use in the treatment of iron deficiency anaemia of iron complexes containing ligands present in certain of the zinc complexes of the present invention has been described in UK patent application Ser. No. 8308053, published as GB No. 2,117,766A, corresponding to U.S. application Ser. No.478,494, now U.S. Pat. No. 4,550,101. However, there has never been any suggestion that the hydroxypyridones contained in the iron complexes described in that application might serve any role in the treatment of zinc depletion. In particular, it will be appreciated that the successful administration of iron and zinc are two quite separate problems as is confirmed by the fact that very many different complexes of iron are marketed for the treatment of iron deficiency anaemia, whilst zinc depletion has in the past been treated with zinc salts.

The zinc complexes of the present invention are of particular interest in that some of the compounds from which the zinc complexes are derived are naturally occurring materials, or are readily derivable from such materials. Furthermore, several of these compounds have previously been used either as the metal-free compound or as its iron complex in foodstuffs, thereby indicating their non-toxic nature and the consequent suitability for pharmaceutical use of the zinc complexes of these compounds.

According to the present invention a pharmaceutical composition comprises a zinc(II) complex in which at least one ligand is provided by a compound being:

(1) 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms; or (2) a 3-hydroxyprid-2-one or 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or, except in the case of ionisable groups, more than one substituent selected from aliphatic acyl, alkoxy, aliphatic amine, aliphatic amide, carboxy, aliphatic ester, halogen, hydroxy and sulpho groups and, optionally, in which one or more of the hydrogen atoms attached to ring carbon atoms are replaced by one of said substituents, by an aliphatic hydrocarbon group of 1 to 6 carbon atoms, or by an aliphatic hydrocarbon group substituted by an alkoxy, aliphatic ester, halogen or hydroxy group; together with a physiologically acceptable diluent or carrier.

The zinc complexes present in the pharmaceutical compositions according to the present invention contain zinc in the divalent state. The zinc complexes are preferably neutral, i.e. there being an internal balance of charges between the metal cation and the ligand(s) bound covalently thereto without the necessity for the presence of a non-covalently bound ion or ions to achieve balance. Moreover, the use of hydroxypyridones containing ionisable substituent groups is of less interest and it is preferred that this internal balance of charges is achieved by complexing with the zinc cation the appropriate number of monobasic, bidentate ligands, such ligands being provided by the hydroxypyrones, and by hydroxypyridones not containing ionisable groups, through the loss of a proton from the hydroxy group (OH→O$^-$). Zinc(II) complexes containing a 2:1 proportion of monobasic, bidentate ligand:zinc(II) are therefore preferred since complexes containing a 1:1 or 3:1 proportion of monobasic, bidentate ligand:zinc(II) require an additional physiologically acceptable ion, for example a chloride anion or a sodium cation, respectively, to establish neutrality. It will be appreciated, however, that although of less interest, the use of such 3:1 and especially 1:1 complexes is not excluded from the invention, particularly when in admixture with the 2:1 complex.

It will be appreciated that zinc complexes may exist in either a tetrahedral or an octahedral form and, although complexes containing a 2:1 proportion of monobasic, bidentate ligand:zinc(II) will usually have the tetrahedral form, it is possible for them to adopt the octahedral form by combination with two additional neutral ligands, in particular water molecules. The preferred 2:1 neutral complexes may therefore be used in either the anhydrous or the dihydrate form, the anhydrous form possibly being converted to the dihydrate form in an in vivo aqueous environment.

Although the complexes according to the present invention are required to contain at least one hydroxypyrone or hydroxypyridone ligand as defined above, they may also contain other ligand(s) derived from an alternative compound which will provide a physiologically acceptable, monobasic, bidentate ligand which is capable of bonding covalently to zinc. The present invention thus includes a zinc(II) complex in which the ligand or each ligand separately is provided by a compound being:

(1) 3-hydroxy-4-pyrone or a 3-hydroxy-4-pyrone as defined hereinbefore;
(2) a 3-hydroxypyrid-2-one or 3-hydroxypyrid-4-one as defined hereinbefore; or
(3) an alternative compound providing a physiologically acceptable, monobasic, bidentate ligand which is capable of bonding covalently to zinc; but with the proviso that at least one of the ligands is of type (1) or (2); together with a physiologically acceptable diluent or carrier.

The preferred complexes according to the present invention containing a 2:1 proportion of monobasic, bidentate ligand:zinc(II) may contain various different combinations of the ligands of the types (1)–(3) described above, subject to the requirement that at least one is a hydroxypyridone or hydroxypyrone ligand. Thus, all of the ligands may be of type (1) or of type (2), although optionally differing within these types, or the ligands may be of two different types, (1) and (3), (2) and (3) or particularly (1) and (2). Complexes of particular interest are those containing two ligands of type (2) or particularly of type (1), these ligands conveniently being identical.

Although complexes containing identical ligands are of particular interest, by virtue of their greater simplicity of preparation and use, complexes containing different ligands do have certain properties which may be of value in particular circumstances. Thus, firstly, the inclusion in a complex of a mixture of different ligands provides an added dimension to the design of complexes having optimised properties for take up in vivo to provide a controlled supply of zinc applicable in a particular human or veterinary context. Secondly, apart from the behaviour of the complexes in vivo, the use of mixed ligand complexes may confer certain advantages in relation to formulation.

As indicated, the hydroxypyrone ligands of type (1) are of particular interest and the complexes according to the present invention may conveniently contain at least one such ligand. The substituted 3-hydroxy-4-pyrones may carry more than one type of aliphatic hydrocarbon group but this is not usual and, indeed, substitution by one rather than two or three aliphatic hydrocarbon groups is preferred. The aliphatic hydrocarbon groups may be cyclic or acyclic, having a branched chain or especially a straight chain in the latter case, and may be unsaturated or especially saturated. Groups of 1 to 4 carbon atoms and particularly of 1 to 3 carbon atoms are of most interest. Alkyl groups are preferred, for example cyclic groups such as cyclopropyl and especially cyclohexyl but, more particularly preferred are acyclic alkyl groups such as n-propyl and isopropyl, and especially ethyl and methyl. Substitution at the 2- or 6-position is of especial interest although, when the ring is substituted by the larger aliphatic hydrocarbon groups, there may be an advantage in avoiding substitution on a carbon atom alpha to the

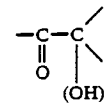

system. This system is involved in the complexing with zinc and the close proximity of one of the larger aliphatic hydrocarbon groups may lead to steric effects which inhibit complex formation.

Examples of hydroxypyrones providing ligands which may be used in complexes according to the present invention have the formula (I), specific hydroxypyrones of particular interest having the formulae (II) and (III):

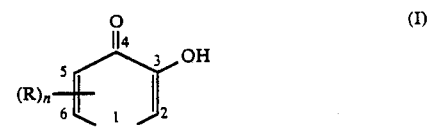

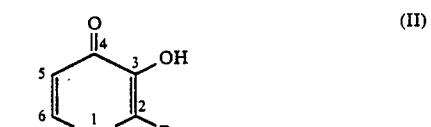

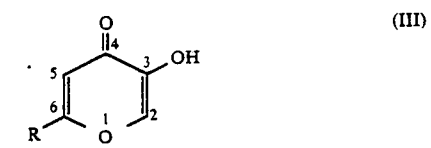

in which R is an alkyl group, for example methyl, ethyl, n-propyl isopropyl to butyl, and n is 0, 1, 2 or 3 (the ring being unsubstituted by any alkyl group when n is 0). Among these compounds 3-hydroxy-2-methyl-4-pyrone (maltol; II, R=CH$_3$) is of most interest, whilst 3-hydroxy-4-pyrone (pyromeconic acid; I, n=0) 3-hydroxy-6-methyl-4-pyrone (isomaltol; III, R=CH$_3$) and particularly 2-ethyl-3-hydroxy-4-pyrone (ethylpyromeconic acid; II, R=C$_2$H$_5$) are also of especial interest.

As regards the hydroxypyridone ligands of type (2), these may be derived from hydroxypyridones of the type described in UK patent application Ser. No. 8308056, published as GB No. 2,118,176A, (corresponding to U.S. application Ser. No. 933,338 or of the type described in UK patent application Ser. No. 8407181, published as GB No. 2,136,807 A (corresponding to U.S. application Ser. No. 592,271, now U.S. Pat. No. 4,585,780). The former consist of a 3-hydoxypyrid-2-one or 3-hydroxypyrid-4-one in which the hydrogen atom attached to the nitrogen atom is replaced by an aliphatic hydrocarbon group of 1 to 6 carbon atoms and, optionally, in which one or more of the hydrogen atoms attached to ring carbon atoms are also replaced by the same or a different aliphatic hydrocarbon group of 1 to 6 carbon atoms, whilst the latter consist of a 3-hydroxypyrid-2-one or 3-hydroxypyrid-4-one which is substituted as defined under (2) hereinbefore but excluding those compounds in which the replacement of hydrogen atoms is effected only by aliphatic hydrocarbon groups these compounds being the substituted hydroxypyridones of the former application). Hydroxypyridones providing ligands which may be used in complexes according to the present invention have the formulae (IV) and (V)

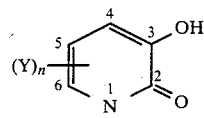
(IV)

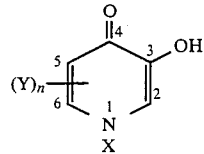
(V)

in which X and Y are substituents as defined hereinbefore and n is 0, 1, 2 or 3, the 3-hydroxypyrid-2-ones generally being of somewhat greater interest than the 3-hydroxypyrid-4-ones.

Preferences as to the nature and position of the substituent groups present in the hydroxypyridones are broadly as expressed in the two earlier applications. Thus, substituted aliphatic hydrocarbon groups present in the hydroxypyridones may as indicated carry more than one substitutent group, except that substitution by more than one ionisable group (amine, carboxy or sulpho) is specifically excluded (substitution by more than one group, only one of which is ionisable not being excluded), but it is preferred that only one substituent group is present. Such substituted aliphatic hydrocarbon group substituents may conveniently contain groups of 1 to 8 and particularly of 1 to 6 carbon atoms, but the simpler hydroxypyridones of UK Patent Application GB No. 2,118,176A containing only unsubstituted aliphatic hydrocarbon group substituents are of the greatest interest. The preferences among the aliphatic hydrocarbon groups present in these hydroxypyridones correspond largely to those expressed in relation to the hydroxypyrones, with methyl groups conveniently being used for substitution on ring carbon atoms but larger alkyl groups also being of particular interest for substitution on the ring nitrogen atoms. Substitution of the ring carbon atoms, which is again preferably by one rather than two or three aliphatic hydrocarbon groups, is of particular interest in the case of the 3-hydroxypyrid-4-ones, for example at the 6- or particularly the 2-position, whilst the 3-hydroxypyrid-2-ones may more often be used without any additional aliphatic hydrocarbon group substituent on the ring carbon atoms. Specific hydroxypyridones of particular interest have formulae (VI), (VII), and (VIII)

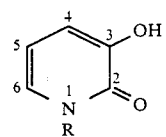
(VI)

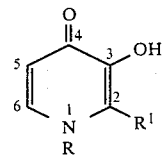
(VII)

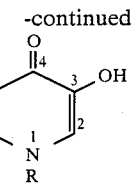
(VIII)

in which R is an alkyl group, for example methyl, ethyl, n-propyl, isopropyl or butyl, and $R^1$ is hydrogen or particularly an alkyl group, for example methyl. Among such compounds 1-ethyl-3-hydroxypyrid-2-one, 3-hydroxy-1-propylpyrid-2-one, 3-hydroxy-1-(2'-methylethyl)-pyrid-2-one, 1-butyl-3-hydroxypyrid-2-one, 1-ethyl-2-methyl-3-hydroxypyrid-4-one, 2-methyl-1-propyl-3-hydroxypyrid-4one, 3-hydroxy-2-methyl-1-(2'-methylethyl)-pyrid-4-one and 1-butyl-3-hydroxy-2-methylpyrid-4-one are of particular interest with the 3-hydroxypyrid-2-ones such as 1-ethyl-3-hydroxypyrid-2-one being especially preferred.

The ligands of type (3) may be derived from various forms of compound, many of which are naturally occurring, and include physiologically acceptable, monobasic, bidentate ligands known in the art. The compounds which provide such ligands will generally comprise (a) a first grouping containing an acidic proton which is lost to provide both the single negative charge on the ligand and also one of its chelating sites and (b) a second grouping which provides the second chelating site. The grouping (a) is preferably either an enolic hydroxy group or a carboxy group whilst the grouping (b) is preferably an amine group, conveniently a primary amino group, or a hydroxy group. In a particular case, one grouping can fulfil both function (a) and function (b). Thus, some monocarboxylic acids can provide an anion capable of a bidentate mode and containing a grouping

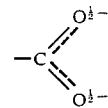

which will fulfil both functions.

Apart from such monocarboxylic acids, for example formic acid, propionic acid and particularly acetic acid, many other forms of acid are of interest for providing type (3) ligands. These include various hydroxy acids, for example lactic acid, gluconic acid, etc., and various amino acids, for example glycine, isoleucine, leucine, methionine, phenylalanine, tyrosine and valine. Also of interest are peptides, particularly the smaller compounds such as tri- and especially di-peptides, for example those containing the same or different amino acids selected from those listed above such as glycyl-leucine, leucyl-glycine and especially glycyl-glycine and leucyl-leucine. Apart from such carboxylic acids, the other group of compounds of particular interest is those containing a grouping

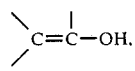

a particular example of this class being ascorbic acid (vitamin C). It should be noted that ascorbic acid is capable of providing a dibasic rather than a monobasic anion but compounds such as this are quite suitable for use in providing ligands of type (3) where they have a single pKa, only, which is less than 10, since in use under physiological conditions, the ascorbate or other such anion will be monobasic. It will be appreciated from the foregoing discussion that the carbohydrate compounds gluconic acid and ascorbic acid are of interest in providing type (3) ligands and this interest extends to other carbohydrates, including particularly the monosaccharide sugars and related compounds. In selecting carbohydrate or other compounds for providing type (3) ligands, the more hydrophobic compounds are generally of greater interest so that among the amino acids, for example, the more complex amino acids than glycine may be of greater value.

Examples of specific zinc(II) complexes according to the present invention are the 2:1 zinc complexes containing two identical ligands drawn from the lists of hydroxypyrones and hydroxypyridones of particular interest given hereinbefore, particularly the hydroxypyrones, for example (maltol)$_2$ zinc(II) and (ethylpyromeconic acid)$_2$ zinc(II). Among complexes containing two different ligands, specific examples are (1-ethyl-3-hydroxypyrid-2-one)(1-butyl-3-hydroxypyrid-4-one) zinc(II), (maltol) (1-ethyl-3-hydroxypyrid-2-one) zinc(II), (maltol)(leucine) zinc(II), (maltol)(glycine) zinc(II), (maltol)(ascorbic acid) zinc(II), (maltol)(gluconic acid) zinc(II) and especially (maltol)(ethylpyromeconic acid) zinc(II). It will be appreciated that "maltol" is used in the names of these complexes to represent the ligand derived from maltol, and similarly for the other ligands, this usage being employed throughout the specification.

In the case of maltol, the preparation of the solid 2:1 zinc maltol complex has been reported in the literature, both in the anhydrous and in the dihydrate form, as part of a study on the nature of the complexes formed by maltol with various divalent cations. In the case of 3-hydroxy-1-methyl-pyrid-4-one and 1-(2'-carboxyethyl)-3-hydroxypyrid-4-one the 2:1 zinc complexes containing two identical ligands have also been prepared, but only in solution, in the context of an investigation of the stability constants of several bivalent metal ions with maltol. In other cases, however, the zinc complexes are believed to be entirely novel and are included, per se, by the present invention.

The zinc complexes are conveniently prepared by the reaction in a suitable mutual solvent of the ligand providing compound(s) and zinc ions, the latter conveniently being derived from a zinc salt, particularly a zinc halide and especially zinc chloride. For the best results, it is preferred to avoid the use of water alone as a reaction solvent, the use of an aqueous/organic solvent mixture or particularly an organic solvent being preferred. The solvent may, for example, be ethanol, methanol or chloroform and mixtures of these solvents together and/or with water where appropriate. In particular, methanol or especially ethanol, or a mixture thereof with chlorofom, may be used where it is desired to effect the separation of at least a major part of a by-product such as sodium chloride by precipitation whilst the zinc complex is retained in solution.

The nature of the product obtained will depend in part upon the molar proportion of the various reactants but also upon the pH of the reaction medium. Thus, for the preparation of 2:1 zinc complexes, for example, the ligand-providing compound(s) and the zinc salt are conveniently mixed in solution in a 2:1 molar proportion and the pH adjusted to a value in the range of 6 to 9, for example 7 or 8. If a similar excess of the compound(s):zinc is employed but no adjustment is made of the acidic pH which results on the admixture of the compound(s) and a zinc salt such as zinc chloride then a mixture of the 2:1 complex or complexes and the 1:1 complex or complexes will be obtained. Adjustment of the pH may conveniently be effected by the addition either of sodium carbonate or of a hydroxide base such as sodium or ammonium hydroxide, the use of a hydroxide base being of particular interest when preparing the zinc complexes in batches of 20 g or more. When using a hydroxide base, the reaction may conveniently be carried out in a medium containing a proportion of water as the solvent, for example in an ethanol: water mixture such as 4:1 v/v ethanol: water, and the pH adjusted by the addition of a 2 molar aqueous solution of the base. It will be appreciated that the presence of water in the reaction mixture will lead to the retention of a by-product in the zinc complex on evaporation of the solvent (a chloride where the zinc salt is zinc chloride). However, this can be removed, if desired, by procedures such as crystallisation from a suitable solvent system where possible or sublimation in the particular case of ammonium chloride. In general, however, the use of a non-aqueous reaction medium in conjunction with sodium carbonate is preferred.

When preparing a 2:1 zinc(II) complex containing different ligands, the individual ligand-providing compounds may conveniently each be used in a 1 molar proportion, together with a 1 molar proportion of the zinc salt. It will be appreciated, however, that the use of such a proportion will not lead exclusively to the mixed 2:1 ligand:zinc(II) complex since, although this form of complex will predominate providing the ligand providing compounds are of similar reactivity, it will be obtained in admixture with the two 2:1 complexes containing identical ligands.

Reaction to form the zinc complex is generally rapid and will usually have proceeded substantially to completion after 5 minutes at about 20° C., although a longer reaction time may be used if necessary. Following separation of any precipitated by-product, such as in the case of certain solvent systems, the reaction mixture may conveniently be evaporated on a rotary evaporator or freeze dried to yield the zinc complex which is usually in solid form. A solid complex may, if desired, be crystallised from a suitable solvent, for example water, an alcohol such as ethanol, or a solvent mixture, including mixtures containing an ether. Whether the zinc complex is obtained in anhydrous or dihydrate form will depend both on the solvent system used for the reaction and on the subsequent working up procedure. Thus rigorous drying may remove the water molecules from a hydrated complex formed in a reaction mixture containing water and recrystallisation from an aqueous medium may add them. If a dihydrate is specifically required, freeze drying of the mixture resulting from the reaction of the ligand-providing compound(s) and a zinc salt such as the chloride or acetate in an aqueous/organic solvent medium may be employed.

Whilst for some uses it may be appropriate to prepare the zinc complex in substantially pure form, i.e. substantially free from by-products of manufacture, in other cases, for example with a solid oral formulation as described hereinafter, the presence of by-products such as sodium chloride may be quite acceptable. In general, however, the neutral 2:1 ligand:zinc(II) complexes in which the ligands are identical are of particular interest in a form which is substantially free at least from those by-products which are complexes containing different overall proportions of the ligand and zinc, in particular the 1:1 complex. When, as discussed hereinafter, it is desired to use the 2:1 zinc complex together with an excess of the metal-free ligand-providing compound(s), this may be achieved by using a greater molar proportion of the compound(s):zinc than 2:1 in the reaction mixture to thereby provide a product containing such an excess.

Certain of the ligand-providing compounds, such as maltol, are available commercialy. With others, routes for their preparation are described in UK Patent Applications GB No. 2,118,176A and GB No. 2,136,807A referred to hereinbefore and in UK patent application Ser. No. 832761 published as GB No. 2,128,998A, relating to hydroxypyrone iron complexes. Thus, for example, with the hydroxypyrones a convenient starting material in many instances consists of pyromeconic acid which is readily obtainable by the decarboxylation of meconic acid and may be reacted with an aldehyde to insert a 1-rydroxyalkyl group at the 2-position, which group may then be reduced to produce a 2-alkyl-3-hydroxy-4-pyrone. The preparation of ethylpyromeconic acid, 2-ethyl-3-hydroxy-4-pyrone, etc., by this mute is described in U.S. application Ser. No. 310,141 (series of 1960).

It will be appreciated that these are not the only routes available to these compounds and their zinc complexes and that various alternatives may be used as will be apparent to those skilled in the art. Moreover, it will be appreciated that certain of the compounds may be converted in vivo to other compounds which are responsible for the activity observed in vivo. This will be true, for example, of compounds containing ester groups which are likely to be converted to carboxy groups when the compounds are administered orally.

The zinc complexes according to the present invention may be formulated for use as pharmaceuticals for both veterinary, for example in an avian or particularly a mammalian context, and especially human use by a variety of methods. For instance, they may be applied as an aqueous, oily or emulsified composition incorporating a liquid diluent which may be employed for parenteral administration and therefore may conveniently be sterile and pyrogen free. Oral administration is often preferred for the treatment of zinc depletion in humans and the complexes of the present invention may be given by such a route. Although compositions incorporating a liquid diluent may be used for oral administration, it is more usual, at least in humans, to use compositions incorporating a solid carrier, for example a conventional solid carrier material such as starch, lactose, dextrin or magnesium stearate. It may even be possible in human and particularly veterinary contexts to use the corresponding metal-free ligand-providing compound or compounds as the solid carrier material or in an extreme instance to use the zinc complex or complexes in solid form as their own carrier. Such solid compositions may conveniently be of a formed type, for example as tablets, capsules (including spansules), etc.

Although solid compositions may be preferred in important contexts such as the oral treatment of zinc depletion in humans, liquid compositions are however of interest in other contexts, for example in veterinary oral administration. In principle liquid formulations of zinc complexes would also be desirable for intramuscular administration in both a veterinary and a human context. In such contexts the complexes containing mixed ligands may have a particular advantage, by virtue of greater solubility, in enabling more concentrated liquid compositions to be prepared.

Other forms of administration than by injection or through the oral route may also be considered in both human and veterinary contexts, for example the use of suppositories or pessaries for human administration.

Compositions may be formulated in unit dosage forms, i.e. in the form of discrete portions containing a unit dose, or a multiple or sub-unit dose. Whilst the dosage of the zinc complex given will depend on various factors, including the particular nature of the complex which is employed in the composition, it may be stated by way of guidance that maintenance at a satisfactory level of the amount of zinc present in the human body will often be achieved using a daily dosage, in terms of the zinc content of the compound, which lies in a range from about 1 to 100 mg and often in a range from 5 to 30 mg, for example 15 mg. (Veterinary doses may be on a similar mg of zinc per kg of body weight basis.) However, it will be appreciated that it may be appropriate under certain circumstances to give daily dosages either below or above these levels. In general, the aim should be to provide the amount of zinc required by the patient without administering any undue excess and the properties of the pharmaceutical compositions according to the present invention are particularly suited to the achievement of this aim. Similarly, the concentration of zinc complex in the pharmaceutical composition may vary quite widely, for example over a range from about 0.01 to about 100% w/w. However, it is more usual for the concentration to exceed 0.1% w/w and it may often exceed 0.5 or 1% w/w, whilst a more usual limit for the upper end of the range is about 50% w/w.

Where desired, more than one zinc complex as described above may be present in the pharmaceutical composition, for example a mixture of the 2:1 maltol:zinc(II) and ethylpyromeconic acid: zinc(II) complexes being used. Other active compounds may also be included in the composition, for example compounds having the ability to facilitate the treatment of zinc depletion. Other components of interest are compounds having the ability to facilitate the treatment of iron deficiency anaemia (in its broadest sense), such as folic acid and, more particularly, a compound providing a source of iron, for example one of those presently marketed for the treatment of iron deficiency anaemia, such as ferrous sulphate, ferrous fumarate, ferrous gluconate, ferrous succinate, ferric EDTA, ferric ascorbate and ferric citrate.

Of particular interest in the context of pharmaceutical compositions containing an iron compound in addition to the zinc complex are those in which this iron compound is an iron complex, particularly a neutral 3:1 iron(III) complex in which the ligands are selected from the same compounds as are discussed hereinbefore for providing the ligands of the zinc complexes. Iron complexes such as this are the subject of UK Patent Applications GB No. 2,117,766A (corresponding to U.S. application Ser. No. 478,494, now U.S. Pat. No. 4,500,101) and GB No. 2,128,998A (corresponding to U.S. applications of Ser. Nos. 542,976 (U.S. Pat. No.

4,575,502), 07/054,086 and 07/073,330, and of UK patent application Ser. No. 8407180, published as GB No. 2,136,806A, (corresponding to U.S. application Ser. No. 592,543, now U.S. Pat. No. 4,650,793) and UK patent application Ser. No. 8410289, published as GB No. 2,156,686A (corresponding to U.S. application Ser. No. 07/178,758). Of special interest amoung these iron complexes are those in which at least one and conveniently all of the ligands derive from a hydroxypyrone. Iron complexes in which each ligand is derived from the same compound are also of especial interest so that the iron complexes in which each ligand is derived from the same hydroxypyrone are preferred. Although the ligands present in the iron complex need not be the same as those present in the zinc complex, there is a particular interest in pharmaceutical compositions in which at least one and conveniently all of the ligands of each iron and zinc complex are derived from hydroxypyrones, particularly one hydroxypyrone for each ligand of the zinc complex and the same or another hydroxypyrone for each ligand of the iron complex. A particularly preferred combination is that of a zinc complex, especially the neutral 2:1 complex, of maltol (3-hydroxy-2-methyl-4-pyrone) or of ethylpyromeconic acid (3-hydroxy-2-methyl-4-pyrone) and an iron complex, especially the neutral 3:1 complex, of maltol or of ethylpyromeconic acid. The combinations may consist of two maltol complexes, two ethylpyromeconic acid complexes or one maltol and one ethylpyromeconic acid complex. Combinations containing both zinc complexes and/or both iron complexes may also be used as may combinations which involve complexes containing mixed maltol and ethylpyromeconic acid ligands.

The daily requirement of iron for the adult human is generally regarded to be 2 to 4 mg whilst that of zinc is 10 to 15 mg. A suitable human daily dosage for the preferred forms of iron complex referred to above is thus somewhat less than the dosage quoted hereinbefore for the zinc complexes being, in terms of the iron content of the complex, in a range from about 0.1 to 10 mg and often in a range from 0.5 to 10 mg, for example 1 or 2 mg, veterinary doses being on a similar g/kg of body weight ratio. However, the relative requirement for zinc and iron can vary quite widely from one patient to another depending on the actual degree of zinc depletion and iron deficiency anaemia exhibited by that patient. As with existing combined mixed iron and zinc preparations, therefore, a range of zinc/iron ratios may be present, for example spanning any combination within the range of 1 part by weight of zinc to 0.25 or 0.4 parts by weight of iron up to 1 part by weight of zinc to 30 or 50 parts by weight of iron. A preferred range is 1 part by weight of zinc to from 1 to 20 parts by weight of iron, for example a 1:7.5 ratio. In general, mixtures containing the higher proportions of zinc are of value when the patient is already exhibiting both zinc depletion and iron deficiency anaemia whilst the lower proportions of zinc are of value when the patient is exhibiting only iron deficiency anaemia but it is desired to avoid any possible zinc depletion.

There are many reports in the literature of the non-specific binding of zinc to cell surfaces and also of a mutual inhibition of bioavailability between zinc and iron. In experiments with radiolabelled zinc in the everted rat jejunum we have found that, in the absence of binding to hydroxypyridone and particularly hydroxypyrone ligands such as maltol and ethylpyromeconic acid, zinc is rapidly removed from the incubation medium by binding to the mucosal surface but that, despite this extensive binding, little permeation occurs. In contrast, when the zinc is bound to such ligands, such non-specific binding is avoided. As discussed hereinafter in more detail, it is desirable, in order to ensure that the zinc is bound, for an excess of the ligand-providing compound to be present, for example to provide a 1:5 or larger molar ratio of zinc:ligand-providing compound or compounds (both bound and unbound), since in the absence of an excess of the compound(s) above the 1:2 molar ratio required to form the 2:1 neutral complex much of the zinc may not in fact be bound. Such non-specific binding may well be associated with the powerful emetic properties of zinc compounds, so that the use of the zinc complexes according to the present invention may well abolish this undesirable side effect. Moreover, studies with radiolabelled iron and zinc in the everted rat jejunum have shown that there is no inhibition on the uptake of zinc from the 2:1 maltol:zinc(II) complex when it is used in admixture with either the 3:1 maltol: iron(III) complex or with ferrous sulphate, nor is there any inhibition on the uptake of iron from the 3:1 maltol: iron(III) complex when it is in admixture with the 2:1 maltol: zinc(II). In each case the avoidance of inhibition is assisted by the presence of excess maltol.

In view of the complicated relationship between iron and zinc the use of the zinc complexes according to the present invention in conjunction with iron complexes containing ligands selected from a similar group of compounds is of particular value in the treatment of iron deficiency anaemia, particularly the rather more complicated forms of anaemia in which both zinc and iron levels are depressed.

When orally administered, zinc is absorbed by the intestine and is transferred via the portal blood stream where it is predominantly bound to apotransferrin. Although the affinity of apotransferrin for zinc is considerably less than that for iron, apotransferrin is rarely saturated with iron and normally carries only about 35% of the possible saturation level. The apotransferrin in the body thus usually has the potential for further metal complexing and the affinity of zinc for apotransferrin, despite being lower than that of iron, is nevertheless quite considerable, the value of $\beta_2$ being 14.6. In order for a zinc complex to donate zinc efficiently with apotransferrin, the $\beta_2$ value for the compound(s) from which the complex is derived should be similar to or less than that of apotransferrin. The affinity of maltol for zinc ($\beta_2 = 9.8$) is therefore such that a complex formed with this compound is very suitable for the oral administration of zinc, since the affinity is relatively high but at the same time is less than that of apotransferrin, thereby allowing the efficient exchange of zinc bound to maltol with apotransferrin. It should be noted that maltol is also suitable for the oral administration of zinc in that it has a lower affinity for calcium ($\beta_2 = 7.2$) than for zinc. Interference with phytic acid, phosphate and tetracycline is predicted to be minimal. Moreover, although the neutral 2:1 maltol:zinc complex is thermodynamically stable; it is also extremely labile and is therefore able to donate zinc to high affinity sites, such as those found in apotransferrin.

It will be appreciated, however, that in addition to possessing properties such as those described above for zinc maltol, a compound which is to act as a source of zinc through oral administration is required to show a high level of membrane permeability. A good indication of the physical properties of a ligand-providing compound and of an zinc complex in this respect is provided by the value of the partition coefficient ($K_{part}$) obtained on partition between n-octanol and Tris hydrochloried (20 mM, pH 7.4; Tris representing 2-amino-2 hydroxymethylpropane 1,3-diol) at 20° C. and expressed as the ratio (concentration in organic phase)/(concentration in aqueous phase). Preferred complexes show a value of $K_{part}$ for each ligand-providing compound of above 0.02 or 0.05 but less than 3.0, especially of above 0.2 but less than 1.0, together with a value of $K_{part}$ for the 2:1 zinc-(II) complex of above 0.02 but less than 6.0, especially of 0.05 or 0.1 to 1.0. The value of $K_{part}$ for maltol is 0.66 and for the neutral 2:1 maltol:zinc complex is 0.11 which values lie in the especially preferred ranges. It will be appreciated, however, that the wide range of ligands which may be present in zinc complexes according to the present invention allows the preparation of complexes having partition coefficients lying throughout the entire ranges given. Thus, for example, a 2:1 complex having a higher partition coefficient than 0.1 may be obtained by using maltol as one ligand and another compound as the second ligand. Alternatively, higher partition coefficients may be obtained, if desired, by the use of hydroxypyrone compounds containing additional and/or larger aliphatic hydrocarbon group substituents on the ring. Thus, for example the values of $K_{part}$ for ethylpyromeconic acid and its 2:1 zinc complex are higher than those for maltol, the higher partition coefficient for the ethyl compound being reflected in the greater uptake of the 2:1 complex in tests on the permeation of erythocytes (further specific data on partition coefficients is to be found in the Examples and, as regards the free compounds, in the earlier applications previously referred to). It should be emphasised, however, that despite the fact that its $K_{part}$ value is not particularly high, the 2:1 complex containing two ligands derived from maltol has proved to be very suitable as an in vivo source of zinc in the tests we have carried out.

Certain aspects of their formulation will enhance the activity of the zinc complexes of the present application in particular contexts. Thus, the preparation of the 2:1 neutral zinc(II) complexes can be effected at neutral pH in essentially quantitative yield using a 2:1 molar proportion of the ligand and a zinc salt, such preparations involving the use of relatively concentrated solutions which preferably contain an organic solvent. However, when a 2:1 ratio of the ligand-providing compound:zinc is present at low concentration, for example $10^{-4}$M, in water at pH 7.4 it has been found that only a small proportion of the zinc will be present as the 2:1 zinc(II) complex, a significant proportion being present as the free metal and the 1:1 complex. Thus, in the case of a 2:1 ratio of maltol:zinc ions the proportion of zinc present as the 2:1 zinc (II) complex under these conditions is only about 15%, about 30% being present as the 1:1 complex and about 50% as the free metal, whilst very little of the 3:1 complex is present. In the presence of a higher ratio of free ligand-providing compound:zinc ions, however, the proportion of zinc present as the 2:1 maltol:zinc(II) complex is much increased, being about 68% for a 10:1 ratio of maltol:zinc and about 82% for a 20:1 ratio. The position is similar with the hydroxypyridone ligands but with a slightly higher proportion of the 2:1 zinc(II) complex at any particular ratio.

The uptake of zinc from complexes according to the present invention will occur primarily from the intestine and it is desirable, for optimum uptake, that the zinc is present in the intestine in the form of the neutral 2:1 zinc(II) complex. This is best achieved by the administration of such a neutral 2:1 complex but it is also necessary for optimum uptake to ensure that this complex does not dissociate to a substantial degree in the intestine. However, at the pH of 7 to 9 prevailing in the small intestine and at low concentrations, the neutral 2:1 complex will be dissociated to form a similar mixture as is described above for a 2:1 ratio of maltol:zinc at a pH of 7.4 (although with a slight increase in the indicated proportion of the 2:1 complex relative to the free metal if the pH is nearer to 9 than 7). The problems posed by this dissociation, which are particularly relevant in the case of the preferred hydroxypyrone ligands, may however be overcome by formulating the 2:1 complex in the presence of the free compound(s) which provide the ligand(s) present in the complex, the dissociation then being opposed through a mass action effect. The extent of this effect is illustrated by the figures quoted above of 15, 68 and 82% for the proportion of zinc present as the 2:1 zinc(II) complex with maltol:zinc ratios of 2:1, 10:1 and 20:1, respectively.

When using a mixture of one 2:1 neutral zinc complex containing two ligands derived from one compound and a second 2:1 neutral zinc complex containing two ligands derived from another compound, it will be usual to combine this mixture together with both ligand-providing compounds in the free form. It will also be usual to use the mixture of both ligand-providing compounds in the free form when the 2:1 neutral zinc complex contains two ligands derived from different compounds. A specific example of such a mixture of complexes and free compounds is the mixture consisting of zinc maltol, zinc ethyl pyromeconic acid, maltol and ethyl pyromeconic acid. A mixture of these compounds in the solid form may either be produced by admixture of the four individual components or directly by reaction of a mixture of an excess maltol and ethylpyromeconic acid with a zinc salt in solution, followed by the isolation of a solid product which will also contain a proportion of the mixed (maltol)(ethylpyromeconic acid) 2:1 neutral zinc complex. Mixtures containing more than one metal-free compound may also be used with advantage when a 2:1 neutral zinc complex containing two ligands derived from one compound is used together with a 3:1 neutral iron complex containing three ligands derived from another compound.

It can be advantageous therefore to include any proportion of the metal-free compound or compounds in admixture with the zinc complexes according to the present invention, particularly the 2:1 neutral complexes, but little further advantage accrues from increasing the proportion beyond a certain level and the administration of large amounts of the free compound or compounds may be physiologically undesirable in certain instances. A preferred range for the molar proportion of the free compound present in compositions according to the present invention which contain a zinc complex in which each ligand is identical is thus from 0 to 100 moles of free compound:1 mole of zinc complex, particularly of the neutral 2:1 zinc complex. Conveniently, a proportion of up to no more than 50, 30 or especially 20 moles:1 mole is used with a lower level of 0.5, 1 or 2 moles:1 mole. A particularly preferred range is from 2 or 3 up to 18 or 20 moles of free compound:1 mole of zinc complex, particularly 2 or 3 up to 8 or 10 moles:1 mole. When there is more than one zinc bound ligand present in the composition, either in the form of a mixed ligand zinc complex and/or of a mixture of zinc complexes, then the proportion of each free ligand-providing compound to the zinc complex containing that ligand may conveniently also fall in the ranges indicated above. It will be appreciated, however, when more than one ligand-providing compound is present it is less likely that the proportion of each will be towards the upper end of the widest range of 0 to 100 moles of free compound: 1 mole of zinc complex, the proportion being more likely to lie in a range of 0.5 to 50 moles:1 mole or such lower ranges as are quoted above. When a iron complex is present containing a different ligand from any present in a zinc complex, it may be advantageous to include in the composition a similar proportion of free compound to iron complex as discussed above for the zinc complexes.

By way of further exemplification it may be stated that a typical composition in unit dosage form may often comprise an amount of zinc complex or complexes containing from 1 to 15 mg of zinc together with a total amount of 20 to 25 mg of the ligand-providing compound or compounds in both free and complexed form, for example 5 mg of zinc with 100 mg of a hydroxypyrone or hydroxypyrone mixture. In the case of mixed zinc complex/iron complex compositions, these may typically contain from 1 to 10 mg of zinc together with 10 to 20 mg of iron and a total amount of 90 to 360 mg of the ligand-providing compound or compounds in both free and complexed form, for example 2 mg of zinc together with 15 mg of iron and 135 mg of a hydroxypyrone or hydroxypyrone mixture.

It will be appreciated that such metal-free compound-/zinc complex mixtures in the proportions described above are novel and that such novel mixtures are included by the present invention.

Zinc complexes according to the present invention, such as the 2:1 neutral zinc (II) maltol complex, are superior when used alone to zinc sulphate which is currently in use for the treatment of zinc depletion, both in relation to absoprtion and to emetic effect. However, it should be stressed that the use of these complexes in admixture with the free ligand-providing compound or compounds leads to an even further improvement with a significantly higher uptake of zinc, and that such mixtures are therefore a very important feature of the present invention.

Before a zinc complex administered orally reaches the intestine it must of course pass through the stomach and, unless steps are taken to prevent it, dissociation of the complex will occur. At the acidic pH of 1 to 3 such as prevails in the stomach a 2:1 complex will be almost completely dissociated to the free metal together with the free ligand-providing compound. The use of the complex in admixture with the metal-free compound(s) in the same way as described above will have similar effect on the dissociation of the zinc complex in the stomach. In contrast with the corresponding iron complexes, however, where a relatively small amount of the free compound(s) can significantly inhibit dissociation under acidic condition, (the presence of the free compound in the proportions previously indicated therefore serving a further function in mixed zinc complex/iron complex formulations), the bias towards the formation of the free metal at a low pH is so marked for the zinc complexes that a significant degree of dissociation will still occur unless a very large proportion of the free compound is used, and this may be undesirable from a physiological point of view in certain instances.

Once it passes from the stomach the dissociated complex should reform in the small intestine if the free metal and the metal-free compound in a suitable proportion are cleared simultaneously from the stomach, particularly if some amount of the free compound is present in the initial formulation. However, it is preferred to formulate the zinc complex in such a way as to prevent or reduce such dissociation (such methods of formulation also having a similar advantageous effect with respect to preventing dissociation of the iron complexes of mixed zinc/iron formulations). In particular, one of several variations may be employed which avoid or reduce exposure of the zinc complex to the acidic conditions of the stomach. Such approaches may involve various types of controlled release system, ranging from one, which may for example be based on a polymer, which simply provides a delayed release of the complex with time, through a system which is resistant to dissociation under acidic conditions, for example by the use of buffering, to a system which is biased towards release under conditions such as prevail in the small intestine, for example a pH sensitive system which is stabilised towards a pH of 1 to 3 such as prevails in the stomach but not one of 7 to 9 such as prevails in the small intestine. Since the pH of the stomach is higher after a meal, it may be advantageous, whatever method of formulation is used, to administer the zinc complexes at such a time.

A particularly convenient approach to a controlled release composition involves encapsulating the zinc complex by a material which is resistant to dissociation in the stomach but which is adapted towards dissociation in the small intestine (or possibly, if the dissociation is slow, in the large intestine). Such encapsulation may be achieved with liposomes, phospholipids generally being resistant to dissociation under acidic conditions. The liposomally entrapped 2:1 zinc(II) complexes can therefore survive the acid environment of the stomach without dissociating. On entry into the small intestine the pancreatic enzymes rapidly destroy the phospholipid-dependent structure of the liposomes thereby releasing the 2:1 complex. Liposome disruption is further facilitated by the presence of bile salts. However, it is usually more convenient to effect the encapsulation, including microencapsulation, by the use of a solid composition of a pH sensitive nature.

The preparation of solid compositions adapted to resist dissociation under acidic conditions but adapted towards dissociation under non-acidic conditions is well known in the art and most often involves the use of enteric coating, whereby tablets, capsules (including spansules), etc., or the individual particles or granules contained therein, are coated with a suitable material. Such procedures are described, for example, in the article entitled "Production of enteric coated capsules" by Jones in Manufacturing Chemist and Aerosol News, May 1970, and in such standard reference books as "Pharmaceutical Dosage Forms", Volume III by Liebermann and Lackmann (published by Marcel Decker). One particular method of encapsulation involves the use of gelatine capsules coated with a cellulose acetate phthalate/diethylphthalate layer. This coating protects the gelatin capsule from the action of water under the acid conditions of the stomach where the coating is protonated and therefore stable. The coating is however destabilised under the neutral/alkaline conditions of the intestine where it is not protonated, thereby allowing water to act on the gelatin. Once released in the intestine the rate of permeation of the intestine wall by the water soluble 2:1 zinc (II) complex is relatively constant irrespective of the position within the intestine, i.e. whether in the jejunum, ileum or large intestine. Other examples of methods of formulation which may be used include the use of polymeric hydrogel formulations which do not actually encapsulate the zinc complex but which are resistant to dissociation under acidic conditions.

It will be appreciated that the present invention involves the first use for medical purposes of the zinc complexes described herein and thus includes a compound being a zinc(II) complex in which at least one of the ligands is provided by a compound being:

(1) 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms;

(2) a 3-hydroxypyrid-2-one or 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or, except in the case of ionisable groups, more than one substituent selected from aliphatic acyl, alkoxy, aliphatic amine, aliphatic amide, carboxy, aliphatic ester, halogen, hydroxy and sulpho groups and, optionally, in which one or more of the hydrogen atoms attached to ring carbon atoms are replaced by one of said substituents, by an aliphatic hydrocarbon group of 1 to 6 carbon atoms, or by an aliphatic hydrocarbon group substituted by an alkoxy, aliphatic ester, halogen or hydroxy group; for use in medicine.

Moreover, the present invention also includes a method for the treatment of a patient, particularly a human or other mammalian patient, which comprises administering such a zinc complex to said patient in order to effect an increase in the levels of zinc in the patient's bloodstream.

In addition to their pharmaceutical use in the treatment of zinc depletion, the zinc complexes of the present invention also have potential for use in other pharmaceutical applications. Various zinc compounds have been shown to have bactericidal and fungicidal properties, being used particularly in dermatological preparations and in preparations for the treatment of infections of the eye. There is also evidence that zinc deficiency is associated with impared wound healing, zinc compounds therefore also having a useful role in this context. However, many of the existing zinc compounds used pharmaceutically have an irritant/astringent action which is undesirable and the zinc complexes of the present invention are of potential value for use in such other pharmaceutical contexts by virtue of their lack of irritancy, astringency and toxicity as compared with the previously used compounds. The zinc complexes of the present invention, including the 3:1 and especially the 1:1 complexes as well as the 2:1 complexes, are thus of marked interest in the treatment of topical reactions involving either bacteria or fungi where there is an overlying inflammatory component and/or delayed wound healing.

For such different pharmaceutical uses various forms of composition as described hereinbefore may be used although compositions suited to localised treatment such as creams, lotions or drops, and including shampoos, are of particular interest. It should be appreciated that the presence of the metal-free ligand-providing compound(s) in such compositions in the proportions discussed hereinbefore may again be of value for the same or other reasons to those previously discussed.

In addition to use in the form of a purely pharmaceutical composition, the zinc complexes described herein are of interest for use as an active ingredient of foodstuffs, particularly for incorporation into the so-called infant formulae for baby feeding. The lack of irritancy/astringency referred to above and the consequent quite acceptable taste of the zinc complexes, for example the 2:1 neutral complexes of zinc maltol and zinc ethylpyromeconic acid, renders them particularly suited to this role.

Such infant formulae are well known, being described for example by Lönnerdal et al in the American Journal of Diseases of the Child, 1983, 137, 433, being based on a human milk substitute such as cow's milk or soy protein and often containing supplies of other metals such as iron, copper and manganese. Of particular interest are foodstuffs which comprise a zinc complex-/iron complex mixture as discussed hereinbefore in view of the lack of mutual inhibitory effect on bioavailability of the metals as previously discussed. It will be appreciated, however, that where the complex(es) contained in the foodstuff are not protected from the acid conditions of the stomach the additional incorporation into the foodstuff of the metal-free compound will be of particular convenience in controlling dissociation, and/or aiding reformation of the complex on clearance from the stomach, a quite large excess of the free compound sometimes being appropriate in these circumstances.

The present invention thus further includes a foodstuff which comprises a nutritional material and a zinc complex as defined hereinbefore.

The invention is illustrated by the following Examples:

EXAMPLES

Example 1

(A) The preparation of zinc maltol

A chloroform solution of maltol [1] is mixed with a 1M solution of zinc chloride in ethanol to provide a 2:1 molar ratio of maltol: zinc in the mixture. After 5 minutes at 20° C., a 10 molar excess of solid sodium carbonate is added and the mixture is stirred for 10 minutes. The mixture is then filtered and the solvent evaporated to give the neutral complex containing maltol and $Zn^{++}$ in a 2:1 proportion. Recrystallisation of the 2:1 complex from ethanol gives a white crystalline solid in essentially quantitative yield, m.p. 203°–204° C. (with decomposition); $\nu_{max}$ (nujol) 1632, 1603 cm$^{-1}$; $\delta(d_6DMSO)$ 7.96 (d, 1H), 6.40 (d, 1H), 2.20 (s, 3H).

[1] The concentration of the maltol is 0.02M although this figure may be varied for this and other hydroxypyrones, for example in a range of 0.01 to 0.5M, being constrained at the upper end of the range by the solubility of the compound in the reaction solvent.

(B) The preparation of zinc ethylpyromeconic acid

The procedure described under (A) is followed with ethylpyromeconic acid in place of maltol to give the neutral 2:1 complex from ethanol as a white crystalline solid in essentially quantitative yield, m.p. 271°–272° C.; $\nu_{max}$ (nujol) 1620, 1560, 1530 cm$^{-1}$; $\delta(d_6DMSO)$ 8.0 (d, 2H), 6.4 (d, 2H), 2.6 (q, 4H), 1.0 (t, 6H).

Example 2

The preparation of (maltol) (ethyl pyromeconic acid) zinc complex

A chloroform solution containing 1 molar equivalent of each of maltol and ethylpyromeconic acid [2] is mixed with a 1M solution of zinc chloride in ethanol to provide a 2:1 molar ratio of ligand-providing compound:zinc in the mixture. After 5 minutes at 20° C., a 10 molar excess of solid sodium carbonate is added and the mixture is stirred for 10 minutes. The mixture is then filtered and the solvent evaporated to give a white crystalline solid containing the neutral 2:1 (maltol) (ethylpyromeconic acid) zinc(II) complex as the predominant product, m.p. 136°–138° C.; $\nu_{max}$ (nujol) 1610, 1570 cm$^{-1}$; $\delta$(d$_6$DMSO) 8.0 (d, 2H), 6.4 (d, 2H), 2.6 (q, 2H), 2.2 (s, 3H), 1.0 (t, 3H). (The solid is not recrystallised as this could lead to a redistribution of the ligands.)

Example 3

(A) The preparation of zinc 1-ethyl-3-hydroxypyrid-2-one

A chloroform solution of 1-ethyl-3-hydroxypyrid-2-one[3] is mixed with a 1M solution of zinc chloride in ethanol to provide a 2:1 molar ratio of hydroxypyridone:zinc in the mixture. After 5 minutes at 20° C., a 10 molar excess of solid sodium carbonate is added and the mixture is stirred for 10 minutes. The mixture is then filtered and the solvent evaporated to give the neutral complex containing the hydroxypyridone and Zn$^{++}$ in a 2:1 proportion. Recrystallisation of the 2:1 complex from ethanol gives a white crystalline solid in essentially quantitative yield, m.p. 200° C. (with decomposition); $\nu_{max}$ (1) 1620 cm$^{-1}$; $\delta$(d$_6$DMSO), 6.80 (q, 1H), 6.30 (m, 2H), 4.01 (q, 2H), 3.3 (s, 3H), 1.23 (t, 3H).

[3] The concentration of the 1-ethyl-3-hydroxypyrid-2-one is 0.02M although this figure may be varied for this and other hydroxypyridones, for example in a range of 0.01 to 0.5M, being constrained at the upper end of the range by the solubility of the compound i the reaction solvent.

(B) The preparation of zinc 3-hydroxy-1,2-dimethylpyrid-4-one

The procedure described under (A) is followed with 3-hydroxy-1,2-dimethylpyrid-4-one in place of 1-ethyl-3-hydroxypyrid-2-one to give the neutral 2:1 complex from ethanol as a white crystalline solid in essentially quantitative yield, m.p. 190° C. (with decomposition); $\nu_{max}$ 1655, 1612 cm$^{-1}$; $\delta$(d$_6$DMSO); 7.53 (d, 1H), 6.20 (d, 1H), 3.70 (s, 3H), 2.33 (s, 3H).

Example 4

Partition data on zinc complexes and on ligand-providing compounds

The partition coefficient $K_{part}$, being the ratio (concentration in n-octanol)/(concentration in aqueous phase) on partition between n-octanol and aqueous tris hydrochloride (20 mM, pH 7.4; Tris represents 2-amino-2-hydroxymethylpropane 1,3-diol), is measured at 20° C. for zinc complexes containing various ligands and for their corresponding ligand-providing compounds as listed in Table 1. In the case of certain of the complexes the partition coefficient for the 2:1 ligand:zinc(II) complex is also measured in the presence of various amounts of the metal-free ligand-providing compound in excess of a 1:2 zinc(II):compound ratio.

In each case, the material is dissolved initially in the aqueous Tris hydrochloride at a concentration of 10$^{-4}$M in relation to zinc. The zinc complexes radiolabelled with $^{65}$Zn are prepared in situ in the buffer by the addition of $^{65}$Zn labelled ZnCl$_2$ to an appropriate amount of the metal-free ligand-providing compound and subsequent adjustment of the pH to 7.4 by the addition of Tris free base. Acid washed glassware is used throughout and, following mixing of 5 ml of the 10$^{-4}$M aqueous solution with 5 ml of n-octanol for 1 minute, the aqueous n-octanol mixture is centrifuged at 1,000 g for 30 seconds. The two resulting phases are separated for a concentration determination. In the case of the ligand-providing compounds the determination is effected by spectrophotometry in the range 220–340 nm whilst in the case of the complexes the determination is effected by counting the $^{65}$Zn.

Results typical of those obtained are shown in Table 1, the partition coefficients being quoted for the first two zinc complexes for different overall ratios of zinc:compound, the first two molar proportions of the compound:zinc being available for binding to the zinc in a 2:1 ligand:zinc(II) complex and the others representing free compound (i.e. a 1:4 zinc(II):compound ratio indicating 1 molar proportion of the 2:1 complex and 2 molar proportions of the free compound if a complete conversion of zinc to the 2:1 complex occurs, although it will be appreciated that not all of the zinc will in fact be present as the 2:1 complex, the proportion in this form being increased by a mass action effect as the proportion of ligand-free compound increases).

By the use of simultaneous equations and the known populations of complexes containing different proportions of zinc: ligand present under the conditions used in this experiment, it is possible to calculate theoretical $K_{part}$ values for neutral 2:1 ligand:zinc(II) complexes of maltol and ethylpyromeconic acid, those being 0.11 and 1.33 respectively as quoted hereinbefore. It will be seen that the value quoted in the Table for a 1:2 zinc(II) compound ratio is in each case considerably less but it will be appreciated that these are measured values which reflect the fact that only a proportion of the maltol or ethylpyromeconic acid is bound to zinc as the 2:1 ligand:zinc (II) complex under these conditions. As the ratio is increased with a consequent increase in the amount of the 2:1 complex which is present, it will be seen that the measured values approach the calculated values.

TABLE 1

| | Partition coefficients | | |
|---|---|---|---|
| | Free | Zinc complex | |
| Ligand-providing compound | compound $K_{part}$ | Zinc:compound molar ratio | $K_{part}$ |
| maltol | 0.66 | 1:2 | 0.038 |
| | | 1:6 | 0.078 |
| | | 1:20 | 0.109 |
| ethylpyromeconic acid | 0.75 | 1:2 | 0.172 |
| | | 1:6 | 0.653 |
| | | 1:20 | 1.241 |
| 3-hydroxy-1-methylpyrid-2-one | 0.44 | 1:2 | 0.13 |
| 1-ethyl-3-hydroxypyrid-2-one | 0.52 | 1:2 | 0.76 |
| 3-hydroxy-1-propylpyrid-2-one | 0.78 | 1:2 | 2.74 |

Example 5

The ability of zinc complexes to donate zinc to apotransferrin

Apotransferrin ($10^{-4}$M) and the $^{65}$Zn radiolabelled zinc complex of maltol (the complex being prepared in situ in the buffer using $^{65}$Zn radiolabelled ZnSO$_4$ at a concentration of $10^{-4}$M and a 10 molar proportion of maltol) were incubated together in Tris hydrochloride (50 mM, buffered to pH 7.4) at 37° C. for 10 minutes when a 1 ml aliquot was removed from the medium and added to a PD10 column. 0.5 ml fractions were collected directly into scintillation vials for counting. The $^{65}$Zn associated with both the apotransferrin and the maltol was estimated and it was found that over 95% of the zinc had been was removed from the zinc complex.

Example 6

In vitro tests on permeation of zinc complexes into human erythrocytes

The accumulation of zinc by human erythrocytes which are associated with the neutral 2:1 ligand:zinc complexes of maltol and ethylpyromeconic acid was studied by incubating for 1 hour at 37° C. a 5% suspension of erythrocytes in a medium consisting of the $^{65}$Zn radiolabelled zinc complex in aqueous sodium chloride (130 mM) buffered to pH 7.4 by 20 mM Tris hydrochloride (2 ml). The zinc complex was formed in situ in the buffered solution using $^{65}$Zn labelled ZnSO$_4$ at a concentration of 0.25 mM together with maltol or ethylpyromeconic acid in a molar ratio of zinc:compound of 1:0, 1:2, 1:5, 1:10 or 1:20, i.e. the concentration of the ligand-providing compound being 0, 0.5, 1.25, 2.5 or 5 mM, respectively. The proportions of 1:2, 1:5, 1:10 and 1:20 provide an increasing amount of the neutral 2:1 zinc(II) complex together with varying amounts of the free compound as explained in Example 4, a small amount of Tris free base (to about 2 mM) being added to avoid an acid pH on reaction to form the complex.

Following the period of incubation, an aliquot of the erythrocyte/medium mixture was placed above a layer of silicone oil and the erythrocytes separated by centrifugation through the oil. The $^{65}$Zn levels associated with the erythrocytes and the incubation medium were then counted. The results obtained are shown in Table 2 where the amount of $^{65}$Zn entering erythrocytes (n.mole per 20 μl of packed erythrocytes) is given, the quoted values being in each case the mean of three determinations. It will be seen that the uptake increases with an increase in the amount of free compound present as the proportion of zinc present as the 2:1 ligand-:zinc(II) complex is increased through the mass action effect.

TABLE 2

| Uptake of zinc complexes by erythrocytes | | |
|---|---|---|
| Ligand-providing compound | Zinc + compound molar:ratio | Uptake of zinc (n.mole) |
| none | 1:0 | 2.0 |
| maltol | 1:2 | 6.7 |
| | 1:5 | 7.9 |
| | 1:10 | 8.5 |
| | 1.20 | 14.4 |
| ethylpyromeconic acid | 1:2 | 8.5 |
| | 1:5 | 20.0 |
| | 1.10 | 28.0 |
| | 1:20 | 35.0 |

Example 7

(A) In vitro tests on permeation of rat jejunal sac by zinc complexes

The zinc uptake into the serosal space of the inverted rat jejunal sac was compared for the neutral 2:1 ligand-:zinc complexes of maltol, ethylpyromeconic acid, 1-ethyl-3-hydroxypyrid-2-one and 3-hydroxy-1-propylpyrid-2-one. Rats (male Sprague Dawley, 60 g) were killed and the jejunum removed, everted and cut into three segments (4 cm length). The segments were tied at both ends and filled with Krebs Ringer buffer (0.2 ml) and incubated in Krebs Ringer buffer containing $^{65}$Zn complexes at 37° C. for periods up to 1 hour (the zinc complexes were prepared in situ at similar concentrations by an analogous procedure to that described in Example 6 but not using any Tris free base). The contents of the sac were counted for $^{65}$Zn, the results obtained being shown in Table 3 where the amount of $^{65}$Zn entering the serosal compartment of the sac is given in n.mole, the quoted values being in each case the mean of three determinations. In the case of the hydroxypyrone ligands it will be seen that the uptake again increases with the increase in the amount of free compound which is present as a result of an increase in the amount of the 2:1 complex which is present.

TABLE 3

| Permeation of rat jejunal sac by zinc complexes | | |
|---|---|---|
| Ligand-providing compound | Zinc:compound molar ratio | Uptake of zinc (n. mole) |
| none | 1:0 | 10.0 |
| maltol | 1:2 | 12.2 |
| | 1:5 | 32.4 |
| | 1:10 | 41.8 |
| | 1:20 | 76.5 |
| ethylpyromeconic acid | 1:10 | 33.4 |
| | 1:20 | 41.9 |
| 1-ethyl-3-hydroxypyrid-2-one | 1:2 | 36.4 |
| | 1:10 | 24.2 |
| 3-hydroxy-1-propylpyrid-2-one | 1:2 | 22.0 |

(B) In vitro tests on permeation of rat jejunal sac by mixtures of zinc and iron The procedure described under (A) is used to study the uptake of zinc from buffer containing a $10^{-3}$M concentration of zinc in the form of $^{65}$Zn radiolabelled zinc sulphate in admixture in a 1:10 molar proportion with maltol, the uptake being measured in the absence of any iron compound, and in the presence of a $10^{-3}$M concentration of iron either as ferrous sulphate or as the 3:1 maltol:iron(III) complex in the presence of free maltol (1:10 overall molar proportion of ferric chloride:maltol).

In an exactly similar manner the uptake of iron from buffer containing a $10^{-3}$M concentration of iron in the form of $^{59}$Fe labelled ferric chloride in admixture in a 1:10 molar proportion with maltol is studied. The uptake is measured in the absence of any zinc compound and in the presence of $10^{-3}$M zinc either as zinc sulphate or as the 2:1 maltol:zinc(II) complex in the presence of free maltol (1:10 overall molar proportion of zinc sulphate:maltol).

The contents of the sac are counted for $^{65}$Zn or $^{59}$Fe, the results obtained being shown in Tables 4 and 5 where the amount of zinc or iron entering the serosal compartment of the sac is given in n.mole, the quoted values being in each case the mean of three determinations. It will be seen that in the presence of an excess of the hydroxypyrone ligand-providing compound there is no significant mutual inhibition of the uptake of either iron or zinc from a neutral complex formed with that hydroxypyrone ligand. Although a slight inhibition of iron uptake from iron maltol in admixture with free maltol was observed in the presence of zinc sulphate, this inhibition was not observed in the presence of zinc maltol. (In these various experiments the 1:10 proportion of zinc:maltol is required in order to ensure that a substantial proportion of the metal is bound to the ligand in the form of the neutral 2:1 maltol:zinc(II) complex, and a similar proportion of iron:maltol is employed for conformity).

TABLE 4

Influence of iron on zinc uptake

| Component containing zinc | Component containing iron | Uptake of zinc (n. mole) |
| --- | --- | --- |
| 1:10 zinc(II):maltol | none | 42 |
| 1:10 zinc(II):maltol | iron(II) sulphate | 39 |
| 1:10 zinc(II):maltol | 1:10 iron(III):maltol | 46 |

TABLE 5

Influence of zinc on iron uptake

| Component containing iron | Component containing zinc | Uptake of zinc (n. mole) |
| --- | --- | --- |
| 1:10 iron(III):maltol | none | 44 |
| 1:10 iron(III):maltol | zinc sulphate | 33 |
| 1:10 iron(III):maltol | 1:10 zinc(II):maltol | 45 |

Example 8

In vivo test of action of zinc complexes in the rat

Two rats (300–350 g) were anaesthetised with nembutal (0.25 ml) and then with ether. A mid-line incision was made and the $^{65}Zn$ radiolabelled sample (20 μg Zn, 1 μCi) containing a 1:10 overall molar proportion of zinc sulphate:maltol (prepared as described in Example 5) was passed into the lumen of the duodenum via a small incision. The abdominal wall was then closed with a suture. The animals were sacrificed at 2 and 4 hours, respectively, after the administration of the sample and the various organs were monitored for their $^{65}Zn$ content. Table 6 shows the levels of $^{65}Zn$ present after 2 hours and 4 hours in the various organs as a percentage of the amount of zinc administered. It will be seen that the totals do not amount to 100% since not all organs have been investigated but the assumption may be made that all the zinc not present in the gut washings has been absorbed, even if it has not all been located.

In the experiment, the blood levels of $^{65}Zn$ were found to be highest between 60 and 90 minutes after the intra-duodenal administration of the zinc complex. In the separated blood sample most of the radioactivity was found to be located in the higher molecular weight fraction of the plasma with none in the low molecular weight range indicating that the zinc was binding to plasma proteins (the separation into fraction was effected on a PD10 column.)

TABLE 6

Distribution of zinc in various rat tissues

| Tissue | Amount of zinc as a percentage of the original dose | |
| --- | --- | --- |
| | Rat sacrificed at 2 hours | Rat sacrificed at 4 hours |
| Gut washings | 57.8 | 44.8 |
| Gut wall | 15.1 | 12.1 |
| Bone marrow | 1.3 | 2.0 |
| Liver | 6.4 | 10.4 |
| Kidneys and urine | 1.0 | 2.0 |
| Blood | 2.3 | 2.5 |
| Spleen | 0.2 | 0.4 |
| Heart | 0.1 | 0.2 |
| Skeletal muscle | N.D.[1] | 2.7 |
| Lungs | N.D. | 0.3 |
| Testes | N.D. | 0.1 |
| Brain | N.D. | <0.01 |

[1]N.D. indicates that these values were not determined in the rat sacrificed at 2 hours.

Example 9

Capsule formulation of zinc maltol (A) A preparation of 2:1 maltol:zinc(II) in admixture with maltol (containing 1 part by weight of zinc to 20 parts by weight of maltol) is obtained by mixing 2:1 maltol:zinc(II) prepared as described in Example 1 with maltol in a 1:32 proportion by weight. The resulting preparation is divided into 50 mg quantities and added to standard gelatine capsules (16 × 5 mm), each capsule containing about 2.5 mg of zinc. The capsules are then coated with a cellulose acetate phthalate/diethylphthalate layer (6 mg coat per cm$^2$ of capsule surface) in a small scale procedure analogous to the procedure described by Jones, ibid. Such capsules are resistant to dissociation in the stomach but will undergo dissociation in the intestine.

(B) In an alternative preparation, the mixture of 2:1 maltol: zinc(II) maltol and maltol used in (A) is replaced by a mixture of 2:1 maltol zinc(II), 3:1 maltol:iron(III) and maltol in a 2:23:5 proportion by weight to provide a 2:15:135 proportion by weight of zinc:iron:maltol (bound and unbound). Each capsule contains about 0.65 mg of zinc and 5 mg of iron.

We claim:

1. A zinc(II) complex in which each ligand is provided by the same or a different compound selected from the group consisting of:
   (1) 3-hydroxy-4-pyrone and a 3-hydroxy-4-pyrone in which one or more of the hydrogen atoms attached to ring carbon atoms are replaced by an aliphatic hydrocarbon group of 1 to 6 carbon atoms;
   (2) a 3-hydroxypyrid-2-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; and
   (3) an alternative compound providing a physiologically acceptable, monobasic, bidentate ligand which is capable of bonding covalently to zinc and which (a) contains a first grouping which is an enolic hydroxy group or a carboxy group and a second grouping which is an amine group or a hydroxy group, (b) is a monocarboxylic acid providing an anion containing a group

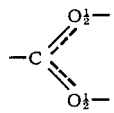

or (c) is a 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; but with the proviso that at least one ligand is of type (1) or (2) and excluding complexes in which the ligand is provided by a compound, or each ligand is provided by the same compound, which is 3-hydroxy-4-pyrone, 3-hydroxy-2-methyl-4-pyrone or 3-hydroxy-6-methyl-4-pyrone.

2. A complex according to claim 1, which is a neutral 2:1 ligand:zinc(II) complex.

3. A zinc(II) complex containing two or three ligands of which at least two are different, each ligand being provided by a compound selected from the group consisting of:
(1) 3-hydroxy-4-pyrone and a 3-hydroxy-4-pyrone in which one or more of the hydrogen atoms attached to ring carbon atoms are replaced by an aliphatic hydrocarbon group of 1 to 6 carbon atoms;
(2) a 3-hydroxypyrid-2-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; and (3) an alternative compound providing a physiologically acceptable, monobasic, bidentate ligand which is capable of bonding covalently to zinc and which (a) contains a first grouping which is an enolic hydroxy group or a carboxy group and a second grouping which is an amine group or a hydroxy group, (b) is a monocarboxylic acid providing an anion containing a group

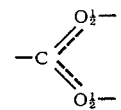

or (c) is a 3-hydroxypyrid-4-one in which the hydrogen atom attached to the nitrogen atom is replaced by an aliphatic acyl group, by an aliphatic hydrocarbon group of 1 to 6 carbon atoms or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; but with the proviso that at least one ligand is of type (1) or (2).

4. A complex according to claim 3, in which the compound of type (3) is formic acid, acetic acid, propionic acid, lactic acid, gluconic acid, ascorbic acid, glycine, leucine, methionine, phenylalanine, tyrosine, valine or a di- and tri-peptide containing the same or different amino acid residues selected from this last mentioned group of six amino acids.

5. A complex according to claim 4, in which the compound of type (3) is gluconic acid, ascorbic acid, glycine or leucine.

6. A complex according to claim 3, in which each ligand is provided by a compound selected from those of types (1) and (2).

7. A complex according to claim 6, in which at least one ligand is provided by a compound of type (1).

8. A complex according to claim 3, in which each ligand is provided by a compound selected from those of type (1).

9. A complex according to claim 8, in which each ligand is provided by a compound selected from 3-hydroxy-4-pyrone and a 3-hydroxy-4-pyrone in which one or more of the hydrogen atoms attached to ring carbon atoms are replaced by an acyclic group of 1 to 4 carbon atoms.

10. A complex according to claim 8, in which each ligand is provided by a compound selected from 3-hydroxy-4-pyrone and a 3-hydroxy-4-pyrone in which one or more of the hydrogen atoms attached to ring carbon atoms are replaced by the same or different substituents selected from methyl, ethyl, n-propyl and isopropyl groups.

11. A complex according to claim 10, in which the substituted 3-hydroxy-4-pyrone has a single substituent at the 2- or 6-position.

12. A complex according to claim 8, in which each ligand is provided by a compound selected from 3-hydroxy-4-pyrone, 3-hydroxy-2-methyl-4-pyrone, 3-hydroxy-6-methyl-4-pyrone, 2-ethyl-3-hydroxy-4-pyrone, 3-hydroxy-2-(1'-methylethyl)-4-pyrone and 3-hydroxy-2-propyl-4-pyrone.

13. A complex according to claim 1, in which each ligand is provided by the same compound of type (1).

14. A neutral 2:1 hydroxypyrone:zinc(II) complex in which each of the two ligands is provided by the same hydroxypyrone being 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms, but excluding 3-hydroxy-4-pyrone, 3-hydroxy-2-methyl-4-pyrone and 3-hydroxy-6-methyl-4-pyrone.

15. A complex according to claim 14, in which the hydroxypyrone is 2-ethyl-3-hydroxy-4-pyrone, 3-hydroxy-2-(1'-methylethyl)-4-pyrone or 3-hydroxy-2-propyl-4-pyrone.

16. The neutral 2:1 hydroxypyrone:zinc(II) complex of 2-ethyl-3-hydroxy-4-pyrone.

17. The neutral 2:1 hydroxypyrone:zinc(II) complex of 3-hydroxy-2-(1'-methylethyl)-4-pyrone or 3-hydroxy-2-propyl-4-pyrone.

18. A complex according to claim 6, in which at least one ligand is provided by a compound of type (2).

19. A complex according to claim 18, in which each ligand is provided by a compound selected from those of type (2).

20. A complex according to claim 1, in which each ligand is provided by the same compound of type (2).

21. A neutral 2:1 hydroxypyridone:zinc(II) complex in which each of the two ligands is provided by the same 3-hydroxypyrid-2-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group.

22. A complex according to claim 21, in which the or each aliphatic hydrocarbon group is an acyclic group of 1 to 4 carbon atoms.

23. A complex according to claim 21, in which the 3-hydroxypyrid-2-one is substituted only on the nitrogen atom, the substituent being selected from methyl, ethyl, n-propyl and isopropyl groups.

24. A complex according to claim 21, in which the 3-hydroxypyridone is 3-hydroxy-1-methylpyrid-2-one, 1-ethyl-3-hydroxypyrid-2-one, 3-hydroxy-1-propylpyrid-2-one or 3-hydroxy-1-(1'-methylethyl)-pyrid-2-one.

25. A mixture of (a) one or more neutral 2:1 ligand:zinc(II) complexes in which each ligand is provided by the same or a different compound selected from the group consisting of:
    (1) 3-hydroxy-4-pyrone and a 3-hydroxy-4-pyrone in which one or more of the hydrogen atoms attached to ring carbon atoms are replaced by an aliphatic hydrocarbon group of 1 to 6 carbon atoms;
    (2) a 3-hydroxypyrid-2-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; and
    (3) an alternative compound providing a physiologically acceptable, monobasic, bidentate ligand which is capable of bonding covalently to zinc and which (a) contains a first grouping which is an enolic hydroxy group or a carboxy group and a second grouping which is an amine group or a hydroxy group, (b) is a monocarboxylic acid providing an anion containing a group

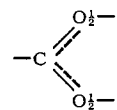

or (c) is a 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; but with the proviso that at least one ligand is of type (1) or (2); and (b) an uncomplexed compound or compounds corresponding to one or more of the ligands in the complex or complexes; the molar proportion of each uncomplexed compound:zinc complex containing that compound being from 0.5:1 to 100:1.

26. A mixture according to claim 25, in which each ligand is provided by the same or a different compound selected from those of types (1) and (2).

27. A mixture according to claim 26, in which each ligand is provided by the same or a different compound selected from those of type (1).

28. A mixture according to claim 27, in which either (a) a single zinc complex containing two identical ligands is present together with the uncomplexed compound corresponding to those ligands or (b) a single zinc complex containing two non-identical ligands or more than one zinc complex is present together with uncomplexed compounds corresponding to each of the ligands present in the complex or complexes.

29. A mixture of (a) one or more neutral 2:1 hydroxypyrone:zinc(II) complexes in which the ligands, which are the same or different, are provided by 3-hydroxy-2-methyl-4-pyrone or 2-ethyl-3-hydroxy-4-pyrone and (b) each ligand-providing compound in uncomplexed form, the molar proportion of each uncomplexed compound:zinc complex containing that compound being from 0.5:1 to 100:1.

30. A mixture according to claim 25, in which the molar proportion of each uncomplexed compound:zinc complex containing that compound is from 2:1 to 20:1.

31. A mixture of (a) a zinc(II) complex in which each ligand is provided by the same or a different compound selected from the group consisting of:
    (1) 3-hydroxy-4-pyrone and a 3-hydroxy-4-pyrone in which one or more of the hydrogen atoms attached to ring carbon atoms are replaced by an aliphatic hydrocarbon group of 1 to 6 carbon atoms;

(2) a 3-hydroxypyrid-2-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; and (3) an alternative compound providing a physiologically acceptable, monobasic, bidentate ligand which is capable of bonding covalently to zinc and which (a) contains a first grouping which is an enolic hydroxy group or a carboxy group and a second grouping which is an amine group or a hydroxy group, (b) is a monocarboxylic acid providing an anion containing a group

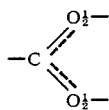

or (c) is a 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; but with the proviso that at least one ligand is of type (1) or (2); and (b) a physiologically acceptable iron complex or iron salt.

32. A mixture of (a) a neutral 2:1 ligand:zinc(II) complex in which each ligand is provided by the same or a different compound selected from the group consisting of:

(1) 3-hydroxy-4-pyrone and a 3-hydroxy-4-pyrone in which one or more of the hydrogen atoms attached to ring carbon atoms are replaced by an aliphatic hydrocarbon group of 1 to 6 carbon atoms;

(2) a 3-hydroxypyrid-2-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, aliphatic amide, aliphatic ester, halogen and hydroxy groups and in which one or more of the hydrogen atoms attached to ring carbon atoms may be replaced by one of said substituents, by an aliphatic hydrocarbon group of 1 to 6 carbon atoms, or by an aliphatic hydrocarbon group substituted by an alkoxy, aliphatic ester, halogen or hydroxy group; and (b) a neutral 3:1 ligand:zinc(III) complex in which each ligand is provided by the same or a different compound as defined under (1) and (2).

33. A mixture according to claim 32, in which each ligand in the zinc and iron complexes is provided by the same or a different compound selected from those of type (1).

34. A mixture according to claim 32, in which the ligands of the iron complex are provided by the same compound or one or more of the same compounds which provide the ligand or ligands present in the zinc complex.

35. A mixture of (a) one or more neutral 2:1 hydroxypyrone:zinc(II) complexes in which the ligands, which are the same or different, are provided by 3-hydroxy-2-methyl-4-pyrone or 2-ethyl-3-hydroxy-4-pyrone, and (b) one or more neutral 3:1 hydroxypyrone:iron(III) complexes in which the ligands, which are the same or different, are provided by 3-hydroxy-2-methyl-4-pyrone or 2-ethyl-3-hydroxy-4-pyrone.

36. A mixture according to claim 32, which additionally contains an uncomplexed compound or compounds corresponding to one or more of the ligands complexed to zinc or iron.

37. A mixture according to claim 36, in which an uncomplexed compound or compounds are present corresponding to each of the ligands complexed to zinc and iron.

38. A mixture according to claim 31, in which the proportion by weight of zinc:iron in the mixture is from 1:0.25 to 1:50.

39. A mixture according to claim 38, in which the proportion is from 1:1 to 1:20.

* * * * *